United States Patent [19]

Detty et al.

[11] 4,365,016

[45] Dec. 21, 1982

[54] BENZOTELLUROPYRYLIUM DIKETONATE ELECTRON ACCEPTING DYE SENSITIZERS FOR ELECTRON DONATING PHOTOCONDUCTIVE COMPOSITIONS

[75] Inventors: Michael R. Detty; Bruce J. Murray; Jerome H. Perlstein, all of Rochester, N.Y.

[73] Assignee: Eastman Kodak Company, Rochester, N.Y.

[21] Appl. No.: 279,363

[22] Filed: Jul. 1, 1981

[51] Int. Cl.$^3$ .................... C07D 345/00; G03C 1/72
[52] U.S. Cl. .................................. 430/83; 260/239 R
[58] Field of Search ...................... 430/83; 260/239 R

[56] References Cited

U.S. PATENT DOCUMENTS 4,123,268 10/1978 Halm .................................. 96/1 PC
4,153,769 5/1979 Halm .................................. 526/195

Primary Examiner—James R. Hoffman
Attorney, Agent, or Firm—John R. Everett

[57] ABSTRACT

Novel benzotelluropyrylium diketonate dyes are disclosed. The dyes are useful in improving the performance of electron donating photoconductive compositions and elements. Methods for making the dye sensitizers are also disclosed.

17 Claims, No Drawings

BENZOTELLUROPYRYLIUM DIKETONATE ELECTRON ACCEPTING DYE SENSITIZERS FOR ELECTRON DONATING PHOTOCONDUCTIVE COMPOSITIONS

FIELD OF THE INVENTION

This invention relates to novel benzotelluropyrylium diketonate dyes, methods of making such dyes and their utility as electron acceptors in electron donating photoconductive compositions and elements.

BACKGROUND OF THE INVENTION

Pyrylium, thiapyrylium and selenapyrylium dyes are known in the prior art. They are known to have a variety of uses including use as electron accepting sensitizers in electron donating photoconductive compositions.

No dyes comprising telluropyrylium nuclei, including benzotelluropyrylium nuclei, have been available for any use. No method for making such dyes has been available heretofore.

SUMMARY OF THE INVENTION

The present invention provides novel dyes which comprise a benzotelluropyrylium diketonate nucleus. The benzotelluropyrylium diketonate nucleus is defined as a 4-H-benzo[b]telluropyrone or 4-H-benzo[b]telluropyrone thione which has a 5-oxo or 5-thio substituent forming a boronate or phosphonate ester involving the hetero atoms at the 4 and 5 positions. The resulting dyes are useful as electron acceptors in increasing the sensitivity of organic photoconductive compositions containing electron donating photoconductors. Tertiary amines such as triarylamine compounds are examples of such photoconductors.

PREFERRED EMBODIMENTS

In a preferred embodiment of this invention the dyes comprise a benzotelluropyrylium diketonate nucleus having the structure:

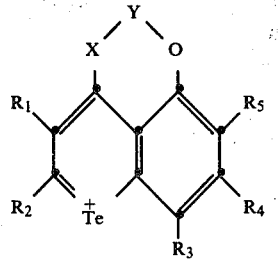

(I).

wherein
$R_2$ represents hydrogen, alkyl, amino, diarylamino, arylamino, alkylamino, dialkylamino, alkoxy, aryl, aryloxy, $-(CH=CH)_{\overline{n}}CH=A_1$ or $-(CH=CH-)_{\overline{n}}A_2$;
$R_1$, $R_3$, $R_4$ and $R_5$ each independently represents hydrogen, alkyl, alkoxy, aryl, aryloxy, halogen, amino, alkylamino, arylamino, dialkylamino or diarylamino;
$A_1$ represents a heterocyclic group containing at least one hetero atom selected from the group consisting of O, S, N, P, Se or Te;
$A_2$ represents alkyl, alkoxy, aryl, diarylamino, dialkylamino, dialkylamino, alkylamino, arylamino or a mono- or polycyclic, heterocyclic group containing at least one hetero atom selected from the group consisting of O, S, N, P, Se or Te; and
n represents 0, 1 or 2;
X represents O or S; and
Y represents $BF_2$ or $PF_4$.

In another preferred embodiment the dyes of this invention comprise a benzotelluropyrylium diketonate nucleus having a structure according to Formula I wherein:
$R_2$ represents hydrogen, phenyl, methyl, 4-methoxyphenyl, 2,5-dimethoxy phenyl, $-(CH=CH)_{\overline{n}}A_2$ or $-(CH=CH)_{\overline{n}}A_1$;
$A_1$ represents 4H-7-methoxy-2-phenyl benzo[b]telluropyranylidene;
$A_2$ represents dimethylamino or 9-julolidyl;
$R_1$, $R_3$, $R_4$ and $R_5$ each independently represents hydrogen or methoxy; and
n represents 0 or 1.

For the purposes of this invention, heteroaryl, heterocyclic and heterocyclylidene groups have hetero atoms such as O, N, S, Se or Te. Examples of the latter groups include the groups generally used to form cyanine dyes, such as pyridyl, furaryl, thiopyranyl, selenopyranyl, telluropyranyl, oxazolyl, thiazolyl, selenazolyl, tellurazolyl, benzoxazolyl, benzthiazolyl, benzselenazolyl or benztellurazolyl. "Alkyl" as a prefix or a suffix refers to a branched- or straight-chain hydrocarbon having up to 16 carbon atoms, such as methyl, butyl, dodecyl, nonyl and isobutyl; "aryl," as a suffix or a prefix, refers to phenyl, naphthyl and anthryl. Heteroaryl, heterocyclidene, alkyl and aryl are optionally further substituted with substituents such as allyl, aryl, halogen, nitro, cyano, carboxy, hydroxy, alkoxy, aryloxy, aralkyl, acyl, amide, sulfonamide, dialkylamine or amino. Halogen refers to Cl, Br, I or F.

The dyes of this invention are prepared from benzotelluropyrone intermediates.

The benzotelluropyrone intermediates are prepared according to the teachings of copending commonly assigned U.S. patent application No. 279,300, entitled "Substituted Benzotelluropyrone Compositions Of Matter," in the name of Detty et al and having the same filing date as the present case. Useful benzotelluropyrone starting materials have the structure:

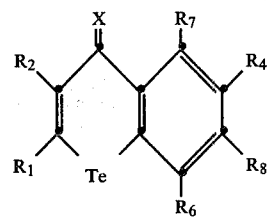

(III)

$R_1$ and $R_2$ each independently represents hydrogen, alkyl, alkoxy, halogen or aryl, or together with the carbon atoms to which they are attached form a mono- or polycyclic, carbocyclic or heterocyclic fused ring structure having about 5 to 20 carbon atoms;
$R_7$ and $R_8$ each independently represents an electron donating group such as hydroxy, alkoxy, aryloxy, amino, dialkylamino, alkylazo, arylazo, halogen, alkylthio, arylthiohydrogen, alkyl or aryl;
$R_4$ represents hydrogen, halogen, alkyl, or $R_4$ and $R_7$, or $R_4$ or $R_8$, together with the carbon atoms to which they are attached, form a mono- or polycyclic, substituted carbocyclic or heterocyclic fused ring structure having about 5 to 20 carbon atoms;

$R_6$ represents hydrogen, halogen, alkyl, or $R_6$ or $R_8$, together with the carbon atoms to which they are attached, form a mono- or polycyclic, carbocyclic or heterocyclic fused ring structure having about 5 to 20 carbon atom and X represents O or S.

Table I presents a representative portion of the dyes made according to one or more of the procedures disclosed in the examples below. The structure of all dyes was confirmed by NMR analysis, infrared spectral analysis, mass spectral analysis and elemental analysis.

TABLE I

Benzotelluropyrylium Diketonates
Electron Accepting Sensitizers

| Dye | Name |
|---|---|
| 1 | 2-Phenylbenzo[b]telluropyrylium-4,5-(difluoroboronate) |
| 2 | 7-Methoxy-2-phenylbenzo[b]telluropyrylium-4,5-(difluoroboronate) |
| 3 | 2-Phenylbenzo[b]telluropyrylium-4S,5-(difluoroboronate) |
| 4 | 7-Methoxy-2-methylbenzo[b]telluropyrylium-4,5-(difluoroboronate) |
| 5 | 7-Methoxybenzo[b]telluropyrylium-4,5-(difluoroboronate) |
| 6 | 2-Methylbenzo[b]telluropyrylium-4,5-(difluoroboronate) |
| 7 | 2-(2,5-dimethoxyphenyl)-7-methoxybenzo[b]telluropyrylium-4,5-(difluoroboronate) |
| 8 | 2-(4-diethylamino-1,3-butadien-1-yl)-7-methoxybenzo[b]telluropyrylium-4,5-(difluoroboronate) |
| 9 | 2-(2-(9-julolidyl)ethenyl)-7-methoxybenzo[b]telluropyrylium-4,5-(difluoroboronate) |
| 10 | 2-(4H—7-methoxy-2-phenylbenzo[b]telluropyran-4-ylidenemethyl)-7-methoxybenzo[b]telluropyrilium-4,5-(difluoroboronate) |

TABLE I-continued

Benzotelluropyrylium Diketonates
Electron Accepting Sensitizers

| Dye | |
|---|---|
| 11 | 2-Phenylbenzo[b]telluro-pyrylium-4,5-(tetra-fluorophosphonate) |
| 12 | 2-(2,5-dimethoxyphenyl)-7-methoxybenzo[b]telluro-pyrylium-4,5-(tetrafluorophosphonate) |

The present invention provides photoconductor compositions and elements in which organic electron donor-type photoconductors are combined with sensitizing amounts of the electron accepting dyes of the present invention.

The compositions are generally prepared by blending a dispersion or solution of the donor type photoconductor together with an electrically insulating, film-forming resin binder, when necessary or desirable, and coating the compositions on a support or forming a self-supporting layer with the photoconductive composition. Generally, a sensitizing amount of the dye compound is mixed with the photoconductive coating composition so that, after thorough mixing, the sensitizing dye is uniformly distributed throughout a layer formed from the composition. The amount of dye added to a photoconductive composition layer to give effective increases in sensitivity varies widely. The optimum concentration in any given case will vary with the specific donor and salt acceptor used.

In general, an appropriate dye is added in a concentration range from about 0.001 to about 30 percent by weight based on the weight of the film-forming coating composition. Generally, the dye is added to the coating composition in an amount from about 0.05 to about 10 percent by weight of the total coating composition.

The dyes used in this invention are effective for enhancing the photosensitivity of a wide variety of donor-type photoconductors especially those containing a tertiary amine component. Useful photoconductors are described below.

(1) arylamine photoconductors including substituted and unsubstituted arylamines, diarylamines, nonpolymeric triarylamines and polymeric triarylamines such as those described in U.S. Pat. Nos. 3,240,597 by Fox issued Mar. 15, 1966, and 3,180,730 by Klupfel et al issued Apr. 27, 1965;

(2) polyarylalkane photoconductors of the types described in U.S. Pat. Nos. 3,274,000 by Noe et al issued Sept. 20, 1966, 3,542,547 by Wilson issued Nov. 24, 1970, and 3,542,544 by Seus et al issued Nov. 24, 1970;

(3) 4-diarylamino-substituted chalcones of the types described by Fox, U.S. Pat. No. 3,526,501 issued Sept. 1, 1970;

(4) nonionic cycloheptenyl compounds of the types described by Looker, U.S. Pat. No. 3,533,786 issued Oct. 13, 1970;

(5) compounds containing an:

nucleus, as described by Fox, U.S. Pat. No. 3,542,546 issued Nov. 24, 1970;

(6) organic compounds having a 3,3'-bisaryl-2-pyrazoline nucleus, as described by Fox et al, U.S. Pat. No. 3,527,602 issued Sept. 8, 1970;

(7) triarylamines in which at least one of the aryl radicals is substituted by either a vinyl radical or a vinylidene radical having at least one active hydrogen-containing group, as described by Brantly et al, U.S. Pat. No. 3,567,450 issued Mar. 2, 1971;

(8) triarylamines in which at least one of the aryl radicals is substituted by an active hydrogen-containing group, as described by Brantly et al, Belgian Pat. No. 728,563 dated Apr. 30, 1969;

(9) any other organic donor compound which exhibits photoconductive properties such as those set forth in Australian Pat. No. 248,402 and the various polymeric photoconductors such as the photoconductive carbazol polymers described in U.S. Pat. No. 3,421,891 issued Jan. 14, 1969.

Preferred binders for use in preparing the photoconductive layers which are sensitized in accordance with the method of this invention comprise polymers having fairly high dielectric strength which are good electrically insulating film-forming vehicles. Materials of this type comprise styrene-butadiene copolymers; silicone resins; styrene-alkyd resins; silicone-alkyd resins; soyaalkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals) such as poly(vinyl butyral); polyacrylic and methacrylic esters such as poly(methyl methacrylate), poly(n-butylmethacrylate), poly(isobutyl methacrylate), etc.; polystyrene; nitrated polystyrene; polymethylstyrene; isobutylene polymers; polyesters such as poly-(ethylene alkylenebis(aryleneoxyalkylene) terephthalate) such as poly(ethylene-co-2,2'-isopropylidenebisphenyleneoxymethylene) terephthalate; phenolformaldehyde resins; ketone resins; polyamides; polycarbonates; polythiocarbonates; 2,2'-isopropylidenebis(phenyleneoxyethylene); nuclear-substituted poly(vinyl haloacrylates), etc. Methods of making resins of this type have been described in the prior art; for example, styrene-alkyd resins are prepared according to the method described in U.S. Pat. Nos. 2,361,019 and 2,258,423. Suitable resins of the type contemplated for use in the photoconductive layers of the invention are sold under such trademarks as Vitel PE-101 ®, Cymac ®, Piccopale 100 ®, Saran ® F-220 and Lexan ® 105 and 145. Other types of binders which are useful in the photoconductive layers of the invention include such materials as paraffine and mineral waxes. If a polymeric photoconductor is used, the binder may be omitted.

The organic coating solvents useful for preparing coating dopes are selected from a variety of materials. Useful liquids are hydrocarbon solvents, including substituted hydrocarbon solvents, with preferred materials being halogenated hydrocarbon solvents. The requisite properties of the solvent are that it be capable of dissolving the acceptor and capable of dissolving or at least highly swelling or solubilizing the polymeric ingredient of the composition. In addition, it is helpful if the solvent is volatile, preferably having a boiling point of less than about 200° C. Particularly useful solvents include halogenated lower alkenes having from 1 to about 3 carbon atoms such as dichloromethane, dichloroethane, dichloropropane, trichloromethane, trichloroethane, tribromomethane, trichlorofluoromethane, trichlorotrifluoroethane, etc.; aromatic hydrocarbons such as benzene, toluene, as well as halogenated benzene compounds such as chlorobenzene, bromobenzene, dichlorobenzene, etc.; ketones such as dialkyl ketones having 1 to about 3 carbon atoms in the alkyl moiety such as dimethyl ketone, methyl ethyl ketone, etc.; and ethers such as tetrahydrofuran, etc. Mixtures of these and other solvents are also useful.

In preparing the photoconductive coating composition, useful results are obtained where the donor is present in an amount equal to at least about 1 weight percent of the coating composition. The upper limit in the amount of donor present can be widely varied in accordance with usual practice. In those cases where a binder is employed, it is generally required that the donor be present in an amount from about 1 weight percent of the coating composition to about 99 percent of the coating composition. A polymeric donor can be employed, in which case an addition binder may not be required. A preferred weight range for the donor substance in the coating composition is from about 10 weight percent to about 60 weight percent.

Suitable supporting materials for coated photoconductive layers sensitized in accordance with the method of this invention include any of a wide variety of electrically conducting supports, for example, paper (at a relative humidity above 20 percent); aluminum-paper laminates; metal foils such as aluminum foil and zinc foil; metal plates such as aluminum, copper, zinc, brass and galvanized plates; vapor-deposited metal layers such as silver, nickel and aluminum coated on paper or conventional photographic film bases such as cellulose acetate and polystyrene. Such conducting materials as nickel can be vacuum-deposited on transparent film supports in sufficiently thin layers to allow electrophotographic elements prepared therewith to be exposed from either side of such elements. An especially useful conducting support is prepared by coating a support material such as poly(ethylene terephthalate) with a conducting layer containing semiconductor dispersed in a resin. Such conducting layers both with and without insulating barrier layers are described in U.S. Pat. No. 3,245,833. Likewise, a suitable conducting coating can be prepared from the sodium salt of a carboxyester lactone of maleic anhydride and a vinyl acetate polymer. Such conducting layers and methods for their optimum preparation and use are disclosed in U.S. Pat. Nos. 3,007,901 and 3,262,807.

Coating thicknesses of the photoconductive composition on the support vary widely. Generally, a coating in the range of about 10 microns to about 300 microns before drying is useful for the practice of this invention. The preferred range of coating thickness is found to be in the range from about 50 microns to about 150 microns before drying, although useful results are obtained outside this range. The resultant dry thickness of the coating is preferably between about 2 microns and about 50 microns, although useful results are obtained with a dry coating thickness between about 1 and about 200 microns.

The elements of the present invention are employed in any of the well-known electrophotographic processes which require photoconductive layers and elements. In one such process, a photoconductive element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by imagewise exposure to light by means of a conventional exposure operation, for example, by a contact-printing technique, or by lens projection of an image to form a latent electrostatic image in the photoconductive layer. Exposing the surface in this manner forms a pattern of electrostatic charge by virtue of the fact that light energy striking the photoconductor causes the electrostatic charge in the light-struck areas to be conducted away from the surface in proportion to the intensity of the illumination in a particular area.

The charge pattern produced by exposure is then developed or transferred to another surface and developed there, i.e., either the charged or uncharged areas rendered visible, by treatment with a medium comprising electrostatically responsive particles having optical density. The developing electrostatically responsive particles can be in the form of a dust, i.e., powder, or a pigment in a resinous carrier, i.e., toner. A preferred method of applying such toner to a latent electrostatic image for solid area development is by the use of a magnetic brush. Methods of forming and using a magnetic brush toner applicator are described in U.S. Pat. Nos. 2,786,439 by Young, 2,786,440 by Giaimo and 2,786,441 by Young, all issued Mar. 26, 1957, and 2,874,063 by Greig issued Feb. 17, 1959. Liquid development of the latent electrostatic image is also useful. In liquid development, the developing particles are carried to the image-bearing surface in an electrically insulating liquid carrier. Methods of development of this type are widely known and have been described in the patent literature, for example, Matcalfe et al, U.S. Pat. No. 2,907,674 issued Oct. 6, 1959. In dry developing processes, the most widely used method of obtaining a permanent record is achieved by selecting a developing particle which has as one of its components a low-melting resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer is made to a second support such as paper which then becomes the final print after development and fusing. Techniques of the type indicated are well-known in the art and have been described in the literature in *RCA Review*, Volume 15 (1954), pages 469–484.

The following examples are presented to illustrate the utility of this invention.

The benzotelluropyrylium boron diketonate compounds of this invention were prepared by reacting a benzotelluropyrone with boron trifluoride etherate or phosphorous pentafluoride in glyme (glycol dimethyl ether).

EXAMPLE 1

Preparation of 2-Phenylbenzotelluropyrylium-4,5-difluoroboron Diketonate (Dye 1, Table I)

2-Phenyl-5-methoxybenzotelluropyrone (0.30 g, 0.83 mmol) was dissolved in 3 ml of boron trifluoride etherate. The resulting solution was warmed on a steam bath for 0.5 hour. After cooling to room temperature, 10 ml of ether was added to the reaction mixture. The dark red solid was collected by filtration and washed with ether. The solid was recrystallized from acetonitrile to give 0.24 g (73%) of red needles.

EXAMPLE 2

Preparation of 2-Phenylmethoxy benzotelluropyrylium-4,5-difluoroboron Diketonate (Dye 2, Table I)

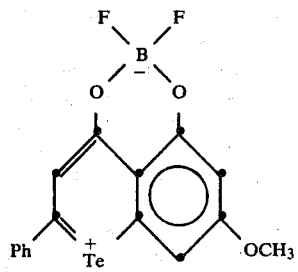

1

5,7-dimethoxy-2-phenyl benzotelluropyrone (0.85 g, 2.2 mmole) was dissolved in 5 ml of boron trifluoride etherate. The resulting solution was warmed on a steam bath for 0.5 hour. After cooling to room temperature, 10 ml of ether was added to the reaction mixture. The dark red solid was collected by filtration and washed with ether (3×25 ml). The solid was recrystallized from acetonitrile to give 0.66 g (72%) of fine, red needles.

The benzotelluropyrylium phosphorous diketonates were prepared according to Example 3.

EXAMPLE 3

Preparation of 2-Phenylbenzotelluorpyrylium-4,5-tetrafluorophosphorous Diketonate (Dye 11, Table I)

2-Phenyl-5-hydroxybenzotelluropyrone (0.20 g, 0.57 mmol) was dissolved in 5 ml of glyme. Phosphorous pentafluoride was bubbled into glyme giving a magenta color and an exothermic reaction. The reaction mixture was chilled precipitating a deep red solid, 0.14 g.

EXAMPLES 4–8

The following illustrative examples show the use of the dyes, of the present invention as sensitizers in electrophotographic elements. Each film was formulated and coated as follows. Specific amounts of a dye sensitizer from Table II and tri-p-tolylamine were dissolved in dichloromethane. A Lexan 145 dichloromethane solution was added to the dye sensitizer (tri-p-tolylamine-dichloromethane solution. Lexan 145 is a polycarbonate available from General Electric. The solution was stirred for several minutes and then coated at 0.006 mil wet thickness on a poly(ethylene terephthalate) support containing 0.4 OD evaporated nickel. After initial evaporation of the solvent, the films were dried 24 hr in air at 60° C. Dry thickness was about 7 μm. Sufficient amounts of the dye sensitizer, tri-p-tolylamine and Lexan 145 were used to prepare coated films containing by weight 2% dye sensitizer, 38% tri-p-tolylamine and 60% Lexan 145. However, the coated films in Example 8 contained 0.5% dye sensitizer and 39.5% tri-p-tolylamine.

The quantum efficiency ($\Phi_o$) of each film was measured as follows. Samples were corona-charged to a surface potential equivalent to the field strengths, $E_o$, indicated in Table II. They were then exposed to monochromatic radiation at a wavelength of ($\lambda$) 350 nm with a bandwidth of 10 nm. The incident photon flux at 350 nm was measured with an Optronics Laboratories Model 730-A Radiometer. Films were allowed to discharge while exposed to the 350-nm radiation. The initial quantum efficiency ($\Phi_o$) (the number of electron-hole pairs produced per incident photon) at field strength $E_o$ was then determined by computation of the slope of the discharge curve at $E_o$. The photodischarge sensitivity at 350 nm ($S_\frac{1}{2}$), was also determined by allowing the films to discharge from $E_o$ to $E_o/2$. The amount of radiation necessary to produce this discharge was then calculated from the time required for this half-decay and the incident photon flux.

Dyes 1, 2, 3, 4 and 11 of Table I were tested as described above. Each of the dyes resulted in an increase in the speed and/or quantum efficiency of the photoconductive layers in which they were included. The quantitative results are presented in Table II below.

TABLE II

| Example No. | Table I Sensitizer | $E_o$ V/cm | $\Phi_o$ | $S_\frac{1}{2}$ ergs/cm$^2$ |
| --- | --- | --- | --- | --- |
|  | Control | 1.6 × 10$^6$ | 0.0094 | 1500 |
| 4 | 1 | 1.3 × 10$^6$ | 0.203 | 30 |
| 5 | 2 | 1.1 × 10$^6$ | 0.169 | 34 |
| 6 | 3 | 2.2 × 10$^5$ | 0.0027 | 239 |
| 7 | 4 | 1.1 × 10$^6$ | 0.18 | 19 |
| 8 | 11 | 8.6 × 10$^5$ | 0.069 | 64 |

Although the invention has been described in considerable detail with particular reference to certain preferred embodiments thereof, variations and modifications can be effected within the spirit and scope of the invention.

We claim:

1. A dye comprising a benzotelluropyrylium diketonate nucleus.

2. A dye comprising a benzotelluropyrylium diketonate nucleus having the structure:

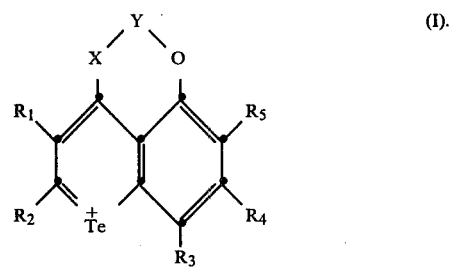

(I).

wherein $R_2$ represents hydrogen, alkyl, amino, diarylamino, arylamino, alkylamino, dialkylamino, alkoxy, aryl, aryloxy, $-(CH=CH)_{\overline{n}}CH=A_1$ or $-(CH=CH)_{\overline{n}}A_2$;

$R_1$, $R_3$, $R_4$ and $R_5$ each independently represents hydrogen, alkyl, alkoxy, aryl, aryloxy, halogen, amino, alkylamino, arylamino, dialkylamino or diarylamino;

$A_1$ represents a heterocyclylidene group containing at least one hetero atom selected from the group consisting of O, S, N, P, Se or Te;

$A_2$ represents alkyl, alkoxy, aryl, diarylamino, dialkylaminoaryl, dialkylamino, alkylamino, arylamino or a mono- or polycyclic, heterocyclic group containing at least one hetero atom selected from the group consisting of O, S, N, P, Se or Te; and n represents 0, 1, or 2;

X represents O or S; and

Y represents $BF_2$ or $PF_4$.

3. A dye as in claim 2 wherein:

$R_2$ represents hydrogen, phenyl, methyl, 4-methoxyphenyl, 2,5-dimethoxy phenyl, $-(CH=CH)_{\overline{n}}A_2$ or $-(CH=CH)_{\overline{n}}CH=A_1$;

$A_1$ represents 4H-7-methoxy-2-phenyl benzo[b]telluropyranylidene;

$A_2$ represents dimethylamino or 9-julolidyl;

$R_1$, $R_3$, $R_4$ and $R_5$ each independently represents hydrogen or methoxy; and n represents 0 or 1.

4. A dye as in claims 1, 2, or 3 selected from the group consisting of:

2-phenylbenzo[b]telluropyrylium-4,5-(difluoroboronate)

2-phenylbenzo[b]telluropyrylium-4,5-(tetrafluorophosphonate)

7-methoxy-2-phenylbenzo[b]telluropyrylium-4,5-(difluoroboronate)

7-methoxy-2-phenylbenzo[b]telluropyrylium-4,5-(tetrafluorophosphonate)

7-methoxy-2-methylbenzo[b]telluropyrylium-4,5-(difluoroboronate)

7-methoxy-2-methylbenzo[b]telluropyrylium-4,5-(tetrafluorophosphonate)

2-phenylbenzo[b]telluropyrylium-4S,5-(difluoroboronate) and 2-(4H-7-methoxy-2-phenylbenzo[b]telluropyranylidene methyl)-7-methoxybenzo[b]telluropyrylium-4,5-(difluoroboronate).

5. A method of making a benzotelluropyrylium boron diketonate dye comprising reacting a benzotelluropyrone with boron trifluoride etherate in glycol dimethyl ether.

6. A method according to claim 5 comprising the step of isolating the resulting benzotelluropyrylium boron diketonate.

7. A method according to claim 5 wherein the benzotelluropyrylium boron diketonate is converted to a benzotelluropyrylium phosphorous diketonate by reacting the benzotelluropyrylium boron diketonate with aqueous sodium bicarbonate and then reacting the product with phosphorous pentafluoride in glycol dimethyl ether.

8. A method as in claim 7 comprising isolating the resulting benzotelluropyrylium phosphorous diketonate.

9. A method of making a benzotelluropyrylium phosphorous diketonate comprising reacting a benzotelluropyrone with phosphorous pentafluoride in glycol dimethyl ether.

10. A method according to claim 9 comprising isolating the resulting benzotelluropyrylium phosphorous diketonate.

11. A photoconductive composition comprising an electron donating organic photoconductor and a sensitizing amount of the benzotelluropyrylium diketonates dyes of claims 1, 2, 3 or 4.

12. A photoconductive composition as in claim 11 wherein the dye is present in an amount of from 0.001 to 30% by weight of the composition.

13. A photoconductive composition as in claim 11 wherein the electron donating photoconductor comprises a tertiary amine.

14. A photoconductive composition as in claim 11 wherein the electron donating photoconductor comprises a triarylamine.

15. A photoconductive composition as in claim 11 wherein the electron donating photoconductor is tri-p-tolylamine.

16. A photoconductive element comprising a support having thereon a layer comprising an electron donating organic photoconductor and a sensitizing amount of the benzotelluropyrylium diketonate dyes of claims 1, 2, 3 or 4.

17. A method of sensitizing electron donating photoconductive compositions comprising the step of adding a sensitizing amount of a benzotelluropyrylium dye of claims 1, 2, 3 or 4 to said photoconductive composition.

* * * * *